United States Patent
Meng et al.

(10) Patent No.: US 12,296,042 B2
(45) Date of Patent: May 13, 2025

(54) COSMETIC COMPOSITIONS COMPRISING SILICONE ELASTOMER

(71) Applicant: Conopco, Inc., Trumbull, CT (US)

(72) Inventors: Sheng Meng, Shanghai (CN); Wenhui Song, Shanghai (CN); Xiaoxia Yang, Shanghai (CN); Joseph Muscat, Warrington (GB); Ashish Anant Vaidya, Bangalore (IN); Jinfang Wang, Shanghai (CN)

(73) Assignee: Conopco, Inc., Hoboken, NJ (US)

( * ) Notice: Subject to any disclaimer, the term of this patent is extended or adjusted under 35 U.S.C. 154(b) by 997 days.

(21) Appl. No.: 17/416,540

(22) PCT Filed: Jan. 6, 2020

(86) PCT No.: PCT/EP2020/050120
§ 371 (c)(1),
(2) Date: Jun. 21, 2021

(87) PCT Pub. No.: WO2020/144130
PCT Pub. Date: Jul. 16, 2020

(65) Prior Publication Data
US 2022/0079869 A1    Mar. 17, 2022

(30) Foreign Application Priority Data

Jan. 10, 2019 (WO) ................ PCT/CN2019/071092
Jan. 28, 2019 (EP) ..................................... 19153926

(51) Int. Cl.
| | | |
|---|---|---|
| *A61K 8/891* | (2006.01) | |
| *A61K 8/35* | (2006.01) | |
| *A61K 8/37* | (2006.01) | |
| *A61K 8/895* | (2006.01) | |
| *A61Q 17/04* | (2006.01) | |

(52) U.S. Cl.
CPC ................ *A61K 8/891* (2013.01); *A61K 8/35* (2013.01); *A61K 8/37* (2013.01); *A61K 8/895* (2013.01); *A61Q 17/04* (2013.01)

(58) Field of Classification Search
CPC . A61K 8/891; A61K 8/35; A61K 8/37; A61K 8/895; A61K 8/585; A61Q 17/04
See application file for complete search history.

(56) References Cited

U.S. PATENT DOCUMENTS 5,811,487 A    9/1998   Schulz, Jr. et al.
2016/0367470 A1   12/2016   Chiou et al.

FOREIGN PATENT DOCUMENTS

| CN | 108025196 | 5/2018 |
| WO | WO2017144530 | 8/2017 |
| WO | WO2017144531 | 8/2017 |
| WO | WO2017211580 | 12/2017 |
| WO | WO2019115169 | 6/2019 |

OTHER PUBLICATIONS

Search Report and Written Opinion in EP19153926; Jun. 13, 2019; European Patent Office (EPO).
Search Report and Written Opinion in PCTEP2020050120; Feb. 12, 2020; World Intellectual Property Org. (WIPO).
IPRP2 in PCTEP2020050120; Mar. 1, 2021; World Intellectual Property Org. (WIPO).
Written Opinion 2 in PCTEP2020050120; Mar. 1, 2021; World Intellectual Property Org. (WIPO).

*Primary Examiner* — Robert A Wax
*Assistant Examiner* — Quanglong N Truong
(74) *Attorney, Agent, or Firm* — Stephanie Huang

(57) ABSTRACT

Disclosed is a cosmetic composition comprising (i) 0.5 to 20 wt % of an organic sunscreen; and (ii) 2 to 60 wt % of a blend comprising a silicone elastomer gel of the Formula (I) and a non-silicone solvent selected from a hydrocarbon, an oil, a modified oil, an ester, an ether, an alcohol or a mixture thereof; wherein the composition comprises less than 1 wt % volatile silicone solvent. Formula (1)

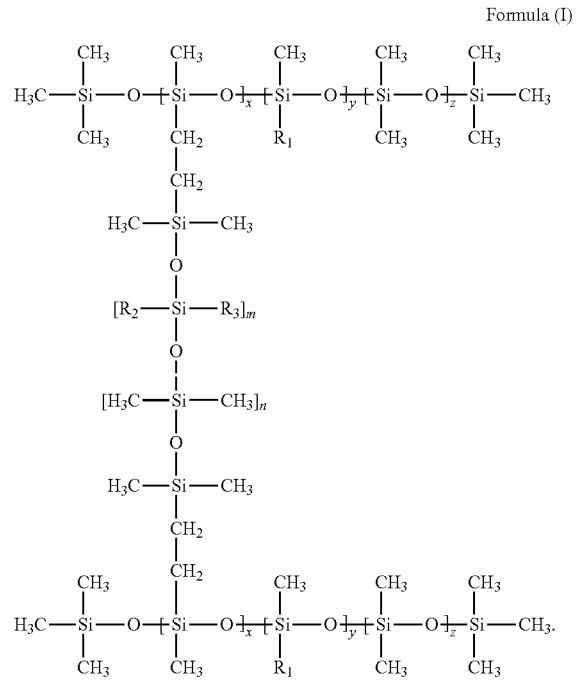

20 Claims, No Drawings

COSMETIC COMPOSITIONS COMPRISING SILICONE ELASTOMER

CROSS REFERENCE TO RELATED APPLICATIONS

The present application is a U.S. National Phase Application under 35 U.S.C. § 371 of International Application No. PCT/EP2020/050120, filed on Jan. 6, 2020, which claims priority to International Application No. PCT/CN2019/071092, filed on Jan. 10, 2019, and European Patent Application No. 19153926.1, filed on Jan. 28, 2019, the contents of which are incorporated herein in their entireties.

TECHNICAL FIELD OF THE INVENTION

The invention concerns a cosmetic composition, especially a cosmetic composition comprising silicone elastomer and sunscreen.

BACKGROUND OF THE INVENTION

Silicone elastomers are included in cosmetic compositions to improve sensorial properties. The term silicone elastomer means cross-linked silicone polymer which swell significantly in a solvent forming a space-filling material which behaves as a visco-elastic soft solid. Generally, the silicone elastomers are dosed in the form of a blend of the elastomer with a cyclic or linear silicone solvent.

To provide sunscreen compositions having high sun protection factor (SPF) and UV-A protection factor (UVAPF), one way is to incorporate more and more amount of UV-A and UV-B sunscreens. However, it is difficult to formulate stable compositions containing such high amount of sunscreens that also comprise silicone elastomers, due to poor compatibility between the two. The structural integrity of the blend comprising the silicone elastomer and the solvent is likely to collapse which may render ineffective the elastomer which as a consequence may no longer provide desired sensorial properties.

WO17211580 A1 (Unilever) discloses cosmetic compositions that comprise blend of a silicone elastomer and a solvent, where the solvent is a volatile silicone oil selected from octamethylcyclotetrasiloxane, decamethylcyclopentasiloxane, dodecamethylcyclohexasiloxane, blends of methyl trimethicone and dimethicone and mixtures thereof and wherein the silicone elastomer has the chemical structure of formula (I). It is disclosed that the composition may additionally comprise an organic sunscreen.

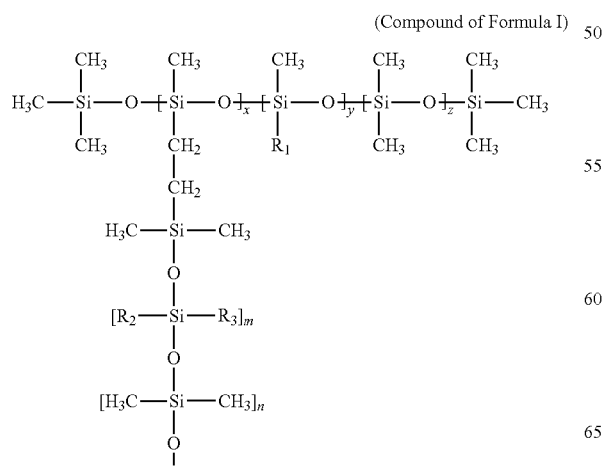

(Compound of Formula I)

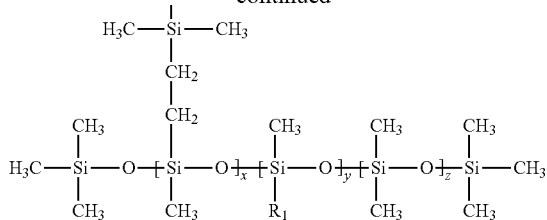

SUMMARY OF THE INVENTION

The present inventors have unexpectedly found that cosmetic compositions comprising an organic sunscreen and a blend comprising a silicone elastomer gel having a particular structure as defined herein and a non-silicone solvent, are stable for prolonged period. This observation provides a reliable method to formulate cosmetic compositions comprising organic sunscreens in more than the usual or the standard amounts in combination with silicone elastomers.

In accordance with a first aspect is disclosed a cosmetic composition comprising:

(i) 0.5 to 20 wt % of an organic sunscreen; and
(ii) 2 to 60 wt % of a blend comprising a silicone elastomer gel of the Formula (I) and a non-silicone solvent selected from a hydrocarbon, an oil, a modified oil, an ester, an ether, an alcohol or a mixture thereof;

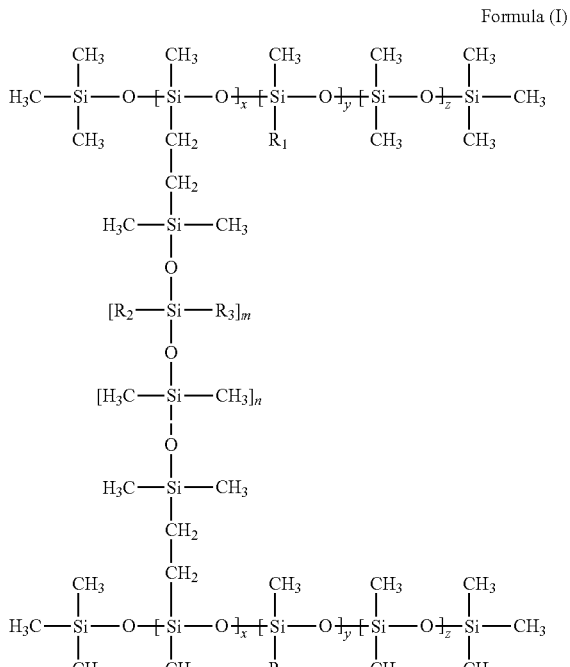

Formula (I)

wherein:
each $R_1$ is independently, $C_{1-36}$ alkyl chain, preferably $C_{8-18}$ alkyl chain;
each $R_2$ is independently, phenyl or $CH_3$;
each $R_3$ is phenyl; and
each x is independently an integer from 3 to 100, preferably from 3 to 20; each y is independently an integer from 1 to 100, preferably from 1 to 20; each z is independently an integer from 1 to 100, preferably from 6 to 50; each m is independently an integer from 1 to 100, preferably from 5 to 30; and each n is independently an integer from 4 to 1000, preferably from 40 to 500, and wherein the composition comprises less than 1 wt % volatile silicone solvent.

In accordance with a second aspect is disclosed a packaged personal care product comprising the cosmetic composition of the first aspect of this invention.

In accordance with a third aspect is a method of providing photoprotection to skin comprising a step of topically applying a cosmetic composition of the first aspect to the skin.

In accordance with a fourth aspect is disclosed use of a composition of the first aspect for photoprotection of the skin.

All other aspects of the present invention will more readily become apparent upon considering the detailed description and examples which follow.

Except in the examples, or where otherwise explicitly indicated, all numbers in this description indicating amounts of material or conditions of reaction, physical properties of materials and/or use may optionally be understood as modified by the word "about".

All amounts are by weight of the cosmetic composition, unless otherwise specified.

It should be noted that in specifying any ranges of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

DETAILED DESCRIPTION

By a cosmetic composition is meant a composition for external application in the form of a leave-on or wash-off format meant for cleaning or care of the skin. Such a composition includes any product applied to a human body for improving appearance, cleansing or general aesthetics. The compositions in accordance with the invention are rinse off-products. Alternatively, and more preferably they are leave-on products. The composition of the present invention may be in the form of a liquid, lotion, cream, foam or gel, or toner, or applied with an implement or via a face mask, pad or patch. "Skin" as used herein is meant to include skin on the face and body (e.g., neck, chest, back, arms, underarms, hands, legs, buttocks and scalp).

Sunscreen

The compositions in accordance with this invention comprise an organic sunscreen.

The organic sunscreen may be a UV-A sunscreen agent selected from a group consisting of dibenzoylmethane or derivatives thereof, a triazine derivative, or benzophenone or a derivative thereof, preferably a derivative of dibenzoylmethane, for example, butyl methoxydibenzoylmethane (sold under the trade name Parsol® 1789).

The organic sunscreen may comprise a UV-B sunscreen agent selected from a group consisting of a benzophenone, an anthranilate, a salicylate, a cinnamate, a camphore, benzylidene malonate, a triazone or a derivative thereof, preferably a cinnamate derivative, for example, ethylhexyl methoxycinnamate (sold under the trade name Parsol® MCX).

Typically, the composition of the present invention comprises from 0.5 to 20% by weight of the organic sunscreen agent, more preferably from 0.5 to 18%, most preferably from 1 to 15%, based on the total weight of the composition.

The Silicone Elastomer Gel

Silicone elastomer gel, as used herein, means cross-linked silicone polymer gel that swells significantly in a non-silicone solvent forming a space filling material which behaves as a visco-elastic soft solid. Alkyl mole content as used herein, means the ratio of moles of alkyl substituted dimethicone units to the total moles of dimethicone units per mole of silicone elastomer unit, unless otherwise specified. The term "gel" as used herein means that the silicone elastomer in the cosmetic compositions of the invention is not particulate.

Phenyl mole content as used herein, means the ratio of moles of phenyl substituted dimethicone units to the total number of dimethicone units per mole of silicone elastomer gel unit, unless otherwise specified.

The silicone elastomer gel has the following formula:

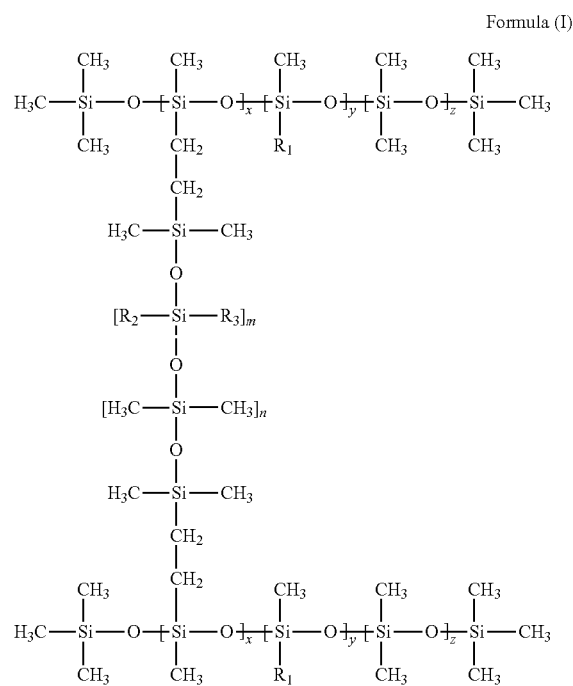

Formula (I)

wherein:
each $R_1$ is independently, $C_{1-36}$ alkyl chain, preferably $C_{8-18}$ alkyl chain;
each $R_2$ is independently, phenyl or $CH_3$;
each $R_3$ is phenyl; and
each x is independently an integer from 3 to 100, preferably from 3 to 20; each y is independently an integer from 1 to 100, preferably from 1 to 20; each z is independently an integer from 1 to 100, preferably from 6 to 50; each m is independently an integer from 1 to 100, preferably from 5 to 30; and each n is independently an integer from 4 to 1000, preferably from 40 to 500.

Silicone elastomer gels suitable for use in the cosmetic compositions of the present invention are functional silicone elastomers that are modified by grafting functional groups onto the backbones of elastomers. It is preferred that the silicone elastomer gel is alkyl modified, phenyl modified or more preferably dual (alkyl and phenyl) modified silicone elastomer gels.

Alkyl modified silicone elastomer gels may be prepared from the reaction of a) a silicone-hydride containing polysiloxane; b) an alkene; and c) a vinyl-terminated dimethylpolysiloxane by using a hydrosilylation catalyst. In the reaction, the alkene reacts with the silicone-hydride containing polysiloxane to form an alkyl modified polysiloxane, which reacts with the vinyl-terminated dimethylpolysiloxane to form the alkyl modified silicone elastomer gel.

When the silicone elastomer gel is alkyl modified or dual modified as disclosed earlier, it is preferred that the alkyl mole content is 0.01 to 0.99, more preferably from 0.02 to 0.20.

Preferably the silicone elastomer gel has the following general formula:

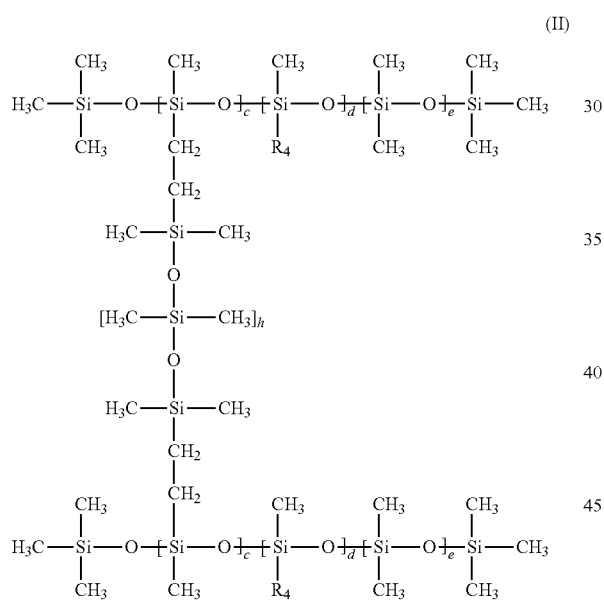

wherein:
each $R_4$ is independently $C_{1-36}$ alkyl chain, preferably $C_{8-18}$; and
each c is independently an integer from 3 to 100, preferably from 3 to 20; each d is independently an integer from 1 to 100, preferably from 1 to 20; each e is independently an integer from 1 to 100, preferably from 6 to 50; and each h is independently an integer from 4 to 1000, preferably from 40 to 500.

Phenyl modified silicone elastomer gel may be prepared from the reaction of a silicone-hydride containing polysiloxane; and a vinyl-terminated dimethyl phenyl polysiloxane by using a hydrosilylation catalyst. Phenyl mole content as used herein, means the ratio of moles of phenyl substituted dimethicone units to the total moles of dimethicone units of the vinyl-terminated dimethyl phenyl polysiloxane. Preferably the phenyl content of the vinyl-terminated dimethyl phenyl polysiloxane is 1 to 50%, more preferably 3 to 30% and most preferably from 7 to 15%. Preferably the phenyl mole content of the phenyl modified silicone elastomer gel is typically in the range from 0.01 to 0.50, more preferably from 0.03 to 0.34.

As an alternative to the structure disclosed as (II) above, a phenyl modified functional silicone elastomer gel has the following preferred general formula:

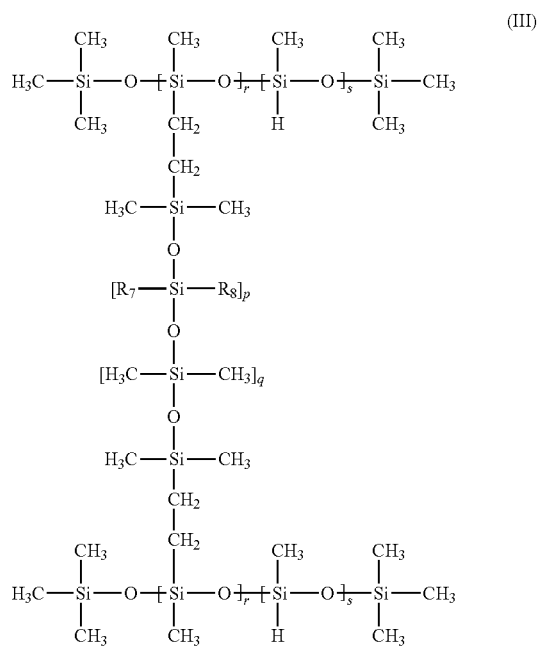

wherein:
each $R_7$ is independently phenyl or $CH_3$;
each $R_8$ is phenyl; and
each r is independently an integer from 3 to 100, preferably from 3 to 20; each s is independently an integer from 2 to 200, preferably from 7 to 70; each p is independently an integer from 1 to 100, preferably from 5 to 30; and each q is independently an integer from 4 to 1000, preferably from 40 to 500.

Dual (alkyl and phenyl) modified silicone elastomer gel may be prepared from the reaction of a silicone-hydride containing polysiloxane; an alkene; and a vinyl-terminated dimethyl phenyl polysiloxane by using a hydrosilylation catalyst.

The alkyl mole content of the dual (alkyl and phenyl) modified silicone elastomer gel is preferably in the range of 0.01 to 0.99, more preferably from 0.02 to 0.20.

The phenyl mole content of the dual (alkyl and phenyl) modified silicone elastomer gel is preferably in the range of 0.01 to 0.50, preferably from 0.03 to 0.34.

It is preferred that the dual (alkyl and phenyl) modified silicone elastomer gel has the general formula:

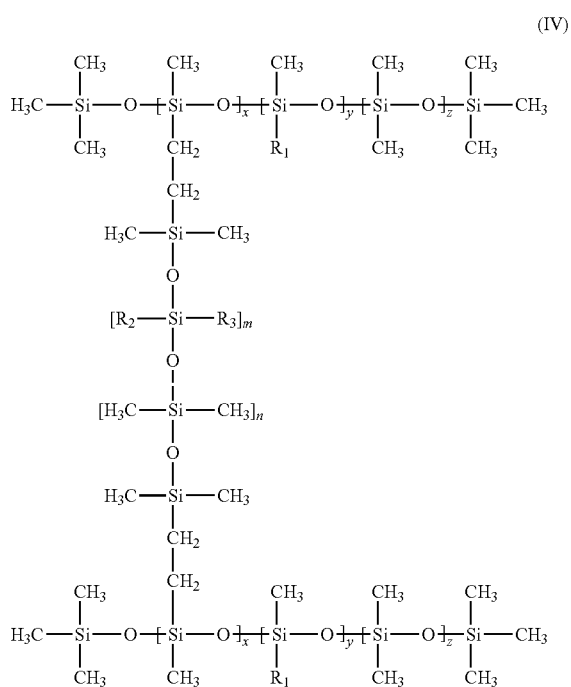

(IV)

wherein:
each $R_1$ is independently $C_{4-36}$ alkyl chain, preferably $C_{8-18}$;
each $R_2$ is independently phenyl or $CH_3$;
each $R_3$ is independently phenyl; and
each x is independently an integer from 3 to 100, preferably from 3 to 20; each y is independently an integer from 1 to 100, preferably from 1 to 20; each z is independently an integer from 1 to 100, preferably from 6 to 50; each m is independently an integer from 1 to 100, preferably from 5 to 30; and each n is independently an integer from 4 to 1000, preferably from 40 to 500.

Further, it is particularly preferred that in the cosmetic compositions of the present invention, the silicone elastomer gel is of the Formula (IV) (i.e., the dual functional elastomer)

The compositions of the present invention comprise less than 5 wt % crosslinked elastomeric silicone polyether, more preferably less than 2 wt %, most preferably less than 1 wt %. The crosslinked elastomeric silicone polyethers and method of preparing such elastomers are disclosed in U.S. Pat. No. 5,811,487 B1.

The compositions of the present invention comprise a non-silicone solvent for the silicone elastomer gel.

Generally, silicone elastomer gels are made available and used in the form of a blend of the silicone elastomer gel and the non-silicone solvent which is a dispersion of the silicone elastomer gel in the non-silicone solvent. The blends of silicone elastomer gel and non-silicone solvent are crosslinked gels that can be prepared by hydrosilylation reaction. The reaction involves low levels of catalyst, usually platinum derivatives, and is generally run into an adequate solvent. Silicone-hydride (SiH) containing silicone polymers are reacted with di-vinyl materials to link independent silicone chains.

The non-silicone solvent for the elastomer gel is a hydrocarbon, an oil, a modified oil, an ester, an ether, an alcohol or a mixture thereof. The non-silicone solvent is preferably a hydrocarbon, more preferably an alkane, most preferably an alkane having a carbon chain length of 8 to 24 carbon atoms. Examples of commercially available non-silicone solvents which are hydrocarbons include Cetiol® Ultimate from BASF which is the mixture of Undecane and Tridecane, EMOSMART® L15 (C13-C15 alkane) and EMOGREEN® L15 (C15-C19 alkane) from Seppic, LexFeel® WOW-DT from Inolex which is Heptyl Undecylenate and C13-C16 Isoparaffin.

Under a shearing force, the elastomer swells in the presence of the non-silicone solvent. Preferably the silicone elastomer gel and the non-silicone solvent for said elastomer are present in the form of a blend of which, the silicone elastomer gel forms 5 to 70 parts by weight of the blend, more preferably from 10 to 60 parts by weight, most preferably from 15 to 40 parts by weight, the balancing being the non-silicone solvent. The reference to parts by weight here is with regard to the blend and not the cosmetic composition which comprises such a blend. In the finished product, for example, in a skincare lotion, it may not be possible to identify that the elastomer and the non-silicone solvent for the elastomer were introduced/added together as a blend but usually when the silicone elastomer is a gel and the non-silicone solvent is also present in the concerned composition, that itself may serve as an indication that when the composition was prepared, the elastomer and the non-silicone solvent were co-dosed and the elastomer is in the form of a gel, as opposed to particulate elastomers which might permit the introduction of the elastomer as such in the form of particles. When the elastomer and the non-silicone solvent for the elastomer are introduced as a blend, the formulation scientist needs to know the solids content of the blend (e.g., 65% solids, 70% solids) so that a calculated amount of the blend can be added to the composition to ensure that the composition contains a desired amount of the elastomer.

The compositions of the present invention comprise 2 to 60 wt %, more preferably 2 to 40 wt % and most preferably 5 to 30 wt % blend of the silicone elastomer gel and the non-silicone solvent for the elastomer.

Other Ingredients

The personal care composition of the invention may be in any form including toners, lotions, creams, mousses, serum or gel that is suitable for topical application to the skin. The cosmetic composition can be either a leave-on or a rinse-off product, preferably a leave-on product, especially a skin care product including skin lotions and skin creams.

The cosmetic composition of the present invention may further comprise 0.1 to 10 wt % of a hydrocarbon emollient. Suitable emollients include wax, cyclic hydrocarbons, straight chain aliphatic hydrocarbons (saturated or unsaturated), and branched chain aliphatic hydrocarbons (saturated or unsaturated).

The cosmetic compositions of the invention preferably comprise a cosmetically acceptable carrier. The carrier may be a liquid or solid material. Typically, carrier forms 10 to 99.9%, more preferably 20 to 95%, most preferably 40 to 85% of the composition. Suitable carrier classes include water, silicones other than the silicone which are covered by the silicone elastomer gel of the Formula (I); polyhydric alcohols, hydrocarbons, and thickening powders.

The cosmetic composition of the invention comprises less than 1 wt % volatile silicone solvent.

In one aspect the cosmetic compositions of the invention are anhydrous. Anhydrous, as used herein, refers to a composition comprises less than 1.5% by weight of water, preferably less than 1.0%.

Alternatively, and more preferably the compositions of the invention comprise 10 to 70 wt %, more preferably 10 to 50 wt % and most preferably 10 to 30 wt % water.

Further preferably the compositions of the invention comprise a skin lightening agent. The skin lightening agent is preferably chosen from one or more of a vitamin B3 compound or its derivative e.g. niacin, nicotinic acid or niacinamide or other well-known skin lightening agents e.g. adapalene, aloe extract, ammonium lactate, anethole derivatives, apple extract, arbutin, azelaic acid, kojic acid, bamboo extract, bearberry extract, *Bletilla tuber, Bupleurum falcatum* extract, burnet extract, butyl hydroxy anisole, butyl hydroxy toluene, citrate esters, Chuanxiong, Dang-Gui, deoxyarbutin, 1,3-diphenyl propane derivatives, 2,5-dihydroxybenzoic acid and its derivatives, 2-(4-acetoxyphenyl)-1,3-dithane, 2-(4-hydroxyphenyl)-1,3-dithane, ellagic acid, escinol, estragole derivatives, Fadeout® (Pentapharm), Fangfeng, fennel extract, *Ganoderma* extract, gaoben, Gatuline Whitening (Gattlefosse), genistic acid and its derivatives, glabridin and its derivatives, gluco pyranosyl-1-ascorbate, gluconic acid, glycolic acid, green tea extract, 4-hydroxy-5-methyl-3[2N-furanone, hydroquinone, 4-hydroxyanisole and its derivatives, 4-hydroxy benzoic acid derivatives, hydroxycaprylic acid, inositol ascorbate, lemon extract, linoleic acid, magnesium ascorbyl phosphate, Melawhite® (Pentapharm), *Morus alba* extract, mulberry root extract, 5-octanoyl salicylic acid, parsley extract, *Phellinus linteus* extract, pyrogallol derivatives, 2,4-resorcinol derivatives, 3,5-resorcinol derivatives, rose fruit extract, salicylic acid, Song-Yi extract, 3,4,5-trihydroxybenzyl derivatives, tranexamic acid, vitamins like vitamin B6, vitamin B12, vitamin C, vitamin A, dicarboxylic acids, resorcinol derivatives, extracts from plants viz. *rubia* and *symplocos*, hydroxycarboxylic acids like lactic acid and their salts e.g. sodium lactate, and mixtures thereof. Vitamin B3 compound or its derivative e.g. niacin, nicotinic acid or niacinamide are the more preferred skin lightening agent as per the invention, most preferred being niacinamide. Niacinamide, when used, is preferably 0.1 to 10 wt %, more preferably 0.2 to 5 wt %.

Other materials which can be included in the cosmetically acceptable carrier include humectants, thickeners and powders. Examples of each of these types of material, which can be used singly or as mixtures, are as follows:

Humectants include those of the polyhydric alcohol-type. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, glycerol, ethoxylated glycerol, propoxylated glycerol and mixtures thereof. The amount of humectant may range, for example, anywhere from 0.5 to 50%, more preferably between 1 and 15% by weight of the composition. Most preferred is glycerol (also known as glycerin). Amounts of glycerin may range, for example, from 0.5% to 50%, more preferably from 1 to 35%, optimally from 2 to 15% by weight of the composition.

A variety of thickening agents may be included in the compositions. Illustrative but not limiting are stearic acid, Acrylamide/Sodium Acryloyldimethyltaurate Copolymer (Aristoflex® AVC), Hydroxyethyl Acrylate/Sodium Acryloyldimethyltaurate Copolymer, Aluminum Starch Octenyl Succinate, Polyacrylates (such as Carbomers including Carbopol® 980, Carbopol® 1342, Pemulen TR-2® and the Ultrez® thickeners), Polysaccharides (including xanthan gum, guar gum, pectin, carageenan and *sclerotium* gums), celluloses (including carboxymethyl cellulose, ethyl cellulose, hydroxyethyl cellulose and methyl hydroxymethyl cellulose), minerals (including talc, silica, alumina, mica and clays, the latter being represented by bentonites, hectorites and attapulgites), magnesium aluminum silicate and mixtures thereof. Amounts of the thickeners may range, for example, from 0.05 to 10 wt %, more preferably from 0.3 to 2 wt % by weight of the composition.

Powders include chalk, talc, Fuller's earth, kaolin, starch, gums, colloidal silica sodium polyacrylate, tetraalkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose and ethylene glycol monostearate.

The cosmetic compositions of the invention may further comprise other ingredients which are common in the art to enhance physical properties and performances. Suitable ingredients include, but are not limited to opacifiers, binders, colorants and pigments, pH adjusting agents, preservatives, optics, perfumes, viscosity modifiers, biological additives, buffering agents, conditioners, natural extracts, essential oils and skin benefit agents including anti-inflammatory agents, cooling agents, antiperspirant agents, anti-aging agents, anti-acne agents, anti-microbial agents and antioxidants.

A wide variety of packaging can be employed to store and deliver the cosmetic compositions. Packaging is often dependent upon the type of personal care end-use. For instance, leave-on skin lotions and creams, shampoos, hair conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively, of the compositions of the invention may be delivered as a stick formulation in a container with propel-repel mechanism where the stick moves on a platform towards a dispensing orifice. Metallic cans pressurized by a propellant and having a spray nozzle serve as packaging for antiperspirants, shave creams and other sprayable personal care products.

In accordance with another aspect is disclosed a method of providing photoprotection to skin comprising a step of topically applying a cosmetic composition of the first aspect to the skin. Preferably the method is non-therapeutic. By non-therapeutic is meant that the method is for cosmetic purpose. Alternatively, the method is therapeutic in nature.

In accordance with another aspect is disclosed use of a cosmetic composition of the first aspect for photoprotection of the skin. Preferably the use is for non-therapeutic purpose. By non-therapeutic is meant that the use is for cosmetic purpose. Alternatively, the use is therapeutic in nature.

The following examples are provided to facilitate an understanding of the present invention. The examples are not provided to limit the scope of the claims.

EXAMPLES

Example 1

Preparation of a Blends of Silicone Elastomer Gel and a Non-Silicone Solvent for the Elastomer Materials:

Silicone-hydride containing polysiloxane (Andisil XL-10), vinyl-terminated dimethylpolysiloxane (Andisil VS-200), vinyl-terminated dimethyl diphenyl polysiloxane (Andisil SF-2430) were purchased from AB Specialty Silicones.

Decamethylcyclopentasiloxane (DC245) was purchased from Dow Corning Corporation. Cetiol® Ultimate (Mixture of C11 and C13 alkane) was purchased from BASF Corporation. All the chemicals were used as received without further purification.

Solids content, as used herein, refers to the weight percentage of silicone elastomers in the blend of silicone elastomer and the non-silicone solvent.

Preparation of a Dual Functional Silicone Elastomer (as in Formula IV) and Cetiol® Ultimate—Blend 16 g Andisil XL-10, 21.8 g dodecene and 44.4 g Cetiol® Ultimate were mixed and stirred in a vial, followed by the addition of 0.118 g platinum complex catalyst. The mixture was stirred at 60° C. for 30 minutes. Then the reaction mixture was transferred to a flask. 730 g Cetiol® Ultimate, 354 g Andisil SF-2430 and 0.28 g platinum complex catalyst were added to the mixture and the mixture was kept at 60° C. with the reflux of water and stirred at 200 rpm for 4 hours. This led to the formation of a silicone elastomer gel in the solvent which could be diluted to different solids contents at 60° C. after the reaction was complete.

Preparation of a Dual Functional Silicone Elastomer (as in Formula IV) and DC 245—Blend 1.02 g Andisil XL-10, 0.94 g dodecene and 4 g DC245 were mixed and stirred in a vial, followed by the addition of 2 µL platinum complex catalyst. The mixture was stirred at 60° C. for 30 minutes. Then the reaction mixture was transferred to a flask. 40 g DC245, 20 g Andisil SF-2430 and 6 µL platinum complex catalyst were added to the mixture and the mixture was kept at 60° C. with the reflux of water and stirred at 200 rpm for 4 hours. This led to the formation of a silicone elastomer gel as per structure (I) in the solvent which could be diluted to different solids contents at 60° C. after the reaction was complete.

Method

Cosmetic compositions in the form of creams were prepared by using the blends (as described above) and certain amount of sunscreens as further described hereinafter.

Details of the compositions comprising silicone elastomer and sunscreen are shown in Table 1. All ingredients are expressed by weight percent by the total composition, and as level of active ingredient, except the silicone elastomer blend.

TABLE 1

| Ingredients | | Composition Ref Code and wt % | |
|---|---|---|---|
| | | 1 | A |
| Silicone elastomer in Cetiol ® Ultimate solvent blend | Silicone elastomer gel | 3.5 | Absent |
| | Cetiol ® Ultimate | 14.0 | |
| Silicone elastomer in DC245 solvent blend | Silicone elastomer gel | Absent | 3.5 |
| | DC245 | | 14.0 |
| Diethylamino Hydroxybenzoyl Hexyl Benzoate (Uvinul ® A Plus from BASF) | | 3.0 | 3.0 |
| Octyl Methoxycinnamate | | 9.0 | 9.0 |
| Caprylic/Capric Triglyceride/(GTCC) | | 2.5 | 2.5 |
| Glycerine | | 7.2 | 7.2 |

TABLE 1-continued

| Ingredients | Composition Ref Code and wt % | |
|---|---|---|
| | 1 | A |
| PEG-10 Dimethicone | 1.2 | 1.2 |
| Water and other minor ingredients | To 100 wt % | To 100 wt % |

In order to determine whether the compositions were stable or not (upon storage under varying conditions), certain tests were performed. Details thereof are described hereinafter.

Amplitude Sweep Rheology Analysis

DV-II PRO Digital Viscometer (from Brookfield Ltd) was used to measure the viscosities of the roll on samples at a consistent shear rate of 10 rpm. This viscometer was connected with PC where an automate program can control the measurement. The values measured after 1 min at a temperature of 25° C. was used. Values are quoted in centipoises (cP=mPa·S) unless otherwise specified.

Stability Test

Stability, as used herein, refers to the concerned composition maintaining its appearance, odor and main structure without phase separation. Samples of the compositions were poured into plastic bottles and filled up to ⅔ of the bottles. Then the samples were stored at 4° C. in a fridge and 50° C. in an oven. For stability test, samples were checked daily. The appearance of samples was observed and recorded. The observation was taken when the samples were still cold/warm and then the samples were left in the fridge/oven for 24 hours before another observation was taken.

The observations pertaining to the compositions of Table 1 are tabulated in Table 2.

TABLE 2

| Composition Ref Code | Viscosity/ cP | Stability | |
|---|---|---|---|
| | | 4° C. (8 weeks) | 50° C. (4 weeks) |
| 1 | 55860 | Stable | Stable |
| A | 40800 | Unstable | Stable |

The unstable formulations are observed as having phase separation (with oil release) while the stable formulation appeared as without any phase separation. It can be seen from the results that samples comprising functional silicone elastomer with non-silicone solvent (Composition 1) are more stable at low temperature compared to the sample comprising functional silicone elastomer with silicone solvent (Composition A), which also indicates functional silicone elastomer with non-silicone solvent can stabilize organic sunscreens, better than functional silicone elastomer with silicone solvent.

The invention claimed is:

1. A cosmetic composition comprising:
   (i) 0.5 to 20 wt % of an organic sunscreen; and
   (ii) 2 to 60 wt % of a blend comprising a silicone elastomer gel of the Formula (I) and a non-silicone solvent comprising a hydrocarbon;

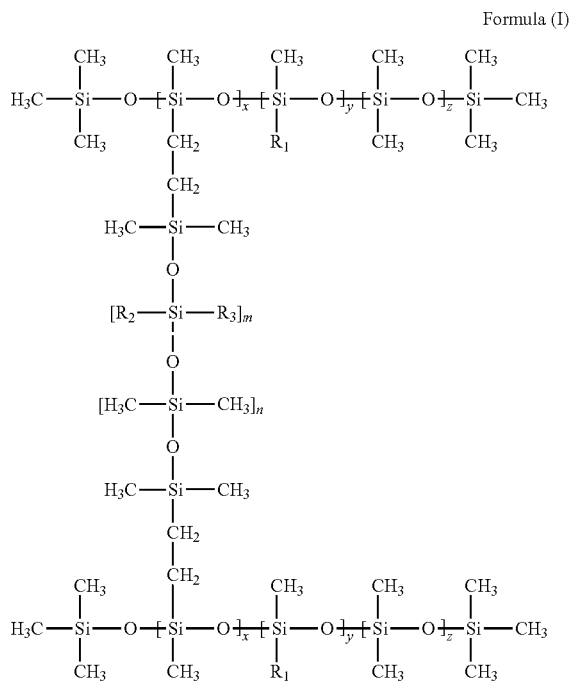

Formula (I)

wherein:
each $R_1$ is independently a $C_{1-36}$ alkyl chain;
each $R_2$ is independently phenyl or $CH_3$;
each $R_3$ is phenyl; and
each x is independently an integer from 3 to 100; each y is independently an integer from 1 to 100; each z is independently an integer from 1 to 100; each m is independently an integer from 1 to 100; and each n is independently an integer from 4 to 1000,
wherein the cosmetic composition comprises less than 1 wt % volatile silicone solvent;
and further wherein the silicone elastomer gel and the non-silicone solvent for the silicone elastomer gel are present in the form of a blend of which the silicone elastomer gel forms 5 to 70 parts by weight of the blend, the balancing being the non-silicone solvent.

2. The cosmetic composition as claimed in claim 1, wherein the non-silicone solvent is an alkane.

3. The cosmetic composition as claimed in claim 1, wherein the hydrocarbon is an alkane having a carbon chain length of 8 to 24 carbon atoms.

4. The cosmetic composition as claimed in claim 1, wherein the organic sunscreen is a UVA sunscreen selected from the group consisting of dibenzoylmethane or derivatives thereof, a triazine derivative, or benzophenone or a derivative thereof.

5. The cosmetic composition as claimed in claim 1, wherein the organic sunscreen is a UVB sunscreen selected from the group consisting of a benzophenone, an anthranilate, a salicylate, a cinnamate, a camphore, benzylidene malonate, a triazone, or a derivative thereof.

6. The cosmetic composition as claimed in claim 1, wherein the $R_1$ of the silicone elastomer gel is a $C_{8-12}$ alkyl group.

7. The cosmetic composition as claimed in claim 6, wherein the $R_2$ of the silicone elastomer gel is a phenyl group.

8. The cosmetic composition as claimed in claim 1, wherein alkyl mole content of the silicone elastomer gel is from 0.01 to 0.99, where alkyl mole content means the ratio of moles of alkyl substituted dimethicone units to the total moles of dimethicone units per mole of the silicone elastomer gel unit.

9. The cosmetic composition as claimed in claim 1, wherein phenyl mole content of the silicone elastomer is from 0.01 to 0.50, where phenyl mole content means the ratio of moles of phenyl substituted dimethicone units to the total moles of dimethicone units per mole of the silicone elastomer gel unit.

10. The cosmetic composition as claimed in claim 1, wherein the silicone elastomer gel forms 10 to 60 parts by weight of the blend, the balance being the non-silicone solvent.

11. A method of providing photoprotection to skin comprising a step of topically applying a cosmetic composition as claimed in claim 1 to the skin.

12. The method as claimed in claim 11, wherein the method is non-therapeutic.

13. The cosmetic composition as claimed in claim 1, wherein the cosmetic composition comprises 0.5 to 18% of the organic sunscreen by weight of the composition.

14. The cosmetic composition as claimed in claim 1, wherein the cosmetic composition comprises 1 to 15% of the organic sunscreen by weight of the composition.

15. The cosmetic composition as claimed in claim 1, wherein each $R_1$ is independently a $C_{8-18}$ alkyl chain; each x of Formula I is independently an integer from 3 to 20; each y is independently an integer from 1 to 20; each z is independently an integer from 6 to 50; each m is independently an integer from 5 to 30; and each n is independently an integer from 40 to 500.

16. The cosmetic composition as claimed in claim 1, wherein the cosmetic composition comprises less than 5 wt % crosslinked elastomeric silicone polyether.

17. The cosmetic composition as claimed in claim 4, wherein the UVA sunscreen is a derivative of dibenzoylmethane.

18. The cosmetic composition as claimed in claim 5, wherein the UVB sunscreen is a cinnamate derivative.

19. The cosmetic composition as claimed in claim 1, wherein the silicone elastomer gel forms 15 to 40 parts by weight of the blend, the balance being the non-silicone solvent.

20. The cosmetic composition as claimed in claim 1, wherein the cosmetic composition comprises 2 to 40 wt % of the blend of the silicone elastomer gel and the non-silicone solvent for the elastomer.

* * * * *